(12) United States Patent
Folden et al.

(10) Patent No.: US 7,892,197 B2
(45) Date of Patent: Feb. 22, 2011

(54) AUTOMATIC PRIME OF AN EXTRACORPOREAL BLOOD CIRCUIT

(75) Inventors: Thomas I. Folden, Alamo, CA (US); Martin Joseph Crnkovich, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 683 days.

(21) Appl. No.: 11/858,104

(22) Filed: Sep. 19, 2007

(65) Prior Publication Data

US 2009/0076433 A1 Mar. 19, 2009

(51) Int. Cl.
*A61M 37/00* (2006.01)
*C02F 1/44* (2006.01)

(52) U.S. Cl. ............... 604/6.11; 604/6.09; 604/6.1; 604/5.04; 604/4.01; 604/5.01

(58) Field of Classification Search ............... 604/5.04, 604/6.06, 6.09, 6.1, 6.11, 6.16
See application file for complete search history.

(56) References Cited

U.S. PATENT DOCUMENTS

| | | | |
|---|---|---|---|
| 1,406,372 A | 2/1922 | Grapp | |
| 1,689,432 A | 10/1928 | Hartwig | |
| 2,107,173 A | 2/1938 | Bauer | |
| 3,130,289 A | 4/1964 | Katzman et al. | |
| 3,605,783 A | 9/1971 | Pecker et al. | |
| 3,694,625 A | 9/1972 | Cole | |
| 3,808,401 A | 4/1974 | Wright et al. | |
| 3,985,135 A | 10/1976 | Carpenter et al. | |
| 4,026,669 A | 5/1977 | Leonard et al. | |
| 4,136,708 A | 1/1979 | Cosentino et al. | |
| 4,370,983 A | 2/1983 | Lichtenstein | |
| 4,459,139 A | 7/1984 | vonReis et al. | |
| 4,508,622 A | 4/1985 | Polaschegg et al. | |
| 4,643,713 A | 2/1987 | Viitala | |
| 4,662,906 A | 5/1987 | Matkovich et al. | |
| 4,676,467 A | 6/1987 | Palsulich | |
| 4,695,385 A | 9/1987 | Boag | |
| 4,778,451 A | 10/1988 | Kamen | |
| 4,808,161 A | 2/1989 | Kamen | |
| 4,826,482 A | 5/1989 | Kamen | |
| 4,869,286 A | 9/1989 | Williams et al. | |

(Continued)

FOREIGN PATENT DOCUMENTS

DE 102005001779 9/2006

(Continued)

OTHER PUBLICATIONS

International Search Report and Written Opinion; PCT/US2008/076751; mailed Jan. 27, 2009.

(Continued)

*Primary Examiner*—Leslie R Deak
(74) *Attorney, Agent, or Firm*—Fish & Richardson P.C.

(57) ABSTRACT

A system for priming an extracorporeal blood circuit is described. The system includes a fluid circuit with an air venting mechanism, a reversible pump, arterial and venous lines, a prime waste bag and a switchable coupler selectively connecting the arterial and venous lines to the waste bag or alternatively interconnecting the arterial and venous lines. A priming fluid is connected to the circuit and circulated in the circuit under different configurations of the arterial and venous line connections.

34 Claims, 8 Drawing Sheets

U.S. PATENT DOCUMENTS

| | | | |
|---|---|---|---|
| 4,902,282 A | 2/1990 | Bellotti et al. | |
| 4,902,877 A | 2/1990 | Grasso et al. | |
| 4,950,134 A | 8/1990 | Bailey et al. | |
| 4,976,162 A | 12/1990 | Kamen | |
| 4,997,464 A | 3/1991 | Kopf | |
| 5,002,471 A | 3/1991 | Perlov | |
| 5,024,756 A | 6/1991 | Sternby | |
| 5,061,236 A | 10/1991 | Sutherland et al. | |
| 5,088,515 A | 2/1992 | Kamen | |
| 5,100,554 A | 3/1992 | Polaschegg | |
| 5,116,021 A | 5/1992 | Faust et al. | |
| 5,146,713 A | 9/1992 | Grafius | |
| 5,178,182 A | 1/1993 | Kamen | |
| 5,193,990 A | 3/1993 | Kamen et al. | |
| 5,211,201 A | 5/1993 | Kamen et al. | |
| 5,241,985 A | 9/1993 | Faust et al. | |
| 5,311,899 A | 5/1994 | Isayama et al. | |
| 5,324,422 A | 6/1994 | Colleran et al. | |
| 5,330,425 A | 7/1994 | Utterberg | |
| 5,344,392 A | 9/1994 | Senninger et al. | |
| 5,350,357 A | 9/1994 | Kamen et al. | |
| D351,470 S | 10/1994 | Scherer et al. | |
| 5,353,837 A | 10/1994 | Faust | |
| 5,395,351 A | 3/1995 | Munsch | |
| 5,421,208 A | 6/1995 | Packard et al. | |
| 5,421,823 A | 6/1995 | Kamen et al. | |
| 5,431,626 A | 7/1995 | Bryant et al. | |
| 5,438,510 A | 8/1995 | Bryant et al. | |
| 5,441,636 A | 8/1995 | Chevallet et al. | |
| 5,447,286 A | 9/1995 | Kamen et al. | |
| 5,474,683 A | 12/1995 | Bryant et al. | |
| 5,486,286 A | 1/1996 | Peterson et al. | |
| 5,540,265 A | 7/1996 | Polaschegg et al. | |
| 5,570,716 A | 11/1996 | Kamen et al. | |
| 5,572,992 A | 11/1996 | Kankkunen et al. | |
| 5,578,070 A | 11/1996 | Utterberg | |
| 5,583,948 A | 12/1996 | Shibayama | |
| 5,591,344 A | 1/1997 | Kenley et al. | |
| 5,614,677 A | 3/1997 | Wamsiedler et al. | |
| 5,628,908 A | 5/1997 | Kamen et al. | |
| 5,634,896 A | 6/1997 | Bryant et al. | |
| 5,640,995 A | 6/1997 | Packard et al. | |
| 5,641,405 A | 6/1997 | Keshaviah et al. | |
| 5,641,892 A | 6/1997 | Larkins et al. | |
| 5,643,205 A | 7/1997 | Utterberg | |
| 5,651,893 A | 7/1997 | Kenley et al. | |
| 5,674,390 A | 10/1997 | Matthews et al. | |
| 5,674,404 A | 10/1997 | Kenley et al. | |
| 5,690,831 A | 11/1997 | Kenley et al. | |
| 5,711,883 A | 1/1998 | Folden et al. | |
| 5,713,865 A | 2/1998 | Manning et al. | |
| 5,714,060 A | 2/1998 | Kenley et al. | |
| 5,725,776 A | 3/1998 | Kenley et al. | |
| 5,741,125 A | 4/1998 | Neftel et al. | |
| 5,755,683 A | 5/1998 | Houle et al. | |
| 5,771,914 A | 6/1998 | Ling et al. | |
| 5,772,637 A | 6/1998 | Heinzmann et al. | |
| 5,776,091 A * | 7/1998 | Brugger et al. | 604/6.1 |
| 5,863,421 A | 1/1999 | Peter, Jr. et al. | |
| 5,925,011 A | 7/1999 | Faict et al. | |
| 5,925,014 A | 7/1999 | Teeple Jr. | |
| 5,938,634 A | 8/1999 | Packard | |
| 5,989,423 A | 11/1999 | Kamen et al. | |
| 5,997,502 A | 12/1999 | Reilly et al. | |
| 6,036,680 A | 3/2000 | Horne et al. | |
| 6,041,801 A | 3/2000 | Gray et al. | |
| 6,042,784 A | 3/2000 | Wamsiedler et al. | |
| 6,065,941 A | 5/2000 | Gray et al. | |
| 6,074,359 A | 6/2000 | Keshaviah et al. | |
| 6,118,207 A | 9/2000 | Ormerod et al. | |
| 6,126,831 A | 10/2000 | Goldau et al. | |
| 6,164,621 A | 12/2000 | Bouchard et al. | |
| 6,165,154 A | 12/2000 | Gray et al. | |
| 6,179,801 B1 | 1/2001 | Holmes et al. | |
| 6,187,199 B1 | 2/2001 | Goldau | |
| 6,196,987 B1 | 3/2001 | Holmes et al. | |
| 6,200,287 B1 | 3/2001 | Keller et al. | |
| 6,220,295 B1 | 4/2001 | Bouchard et al. | |
| 6,223,130 B1 | 4/2001 | Gray et al. | |
| 6,231,537 B1 | 5/2001 | Holmes et al. | |
| 6,234,989 B1 | 5/2001 | Brierton et al. | |
| 6,264,680 B1 * | 7/2001 | Ash | 607/106 |
| 6,280,406 B1 | 8/2001 | Dolecek et al. | |
| 6,316,864 B1 | 11/2001 | Ormerod | |
| 6,336,916 B1 | 1/2002 | Bormann et al. | |
| 6,337,049 B1 | 1/2002 | Tamari | |
| 6,343,614 B1 | 2/2002 | Gray et al. | |
| 6,361,518 B1 | 3/2002 | Brierton et al. | |
| 6,364,857 B1 | 4/2002 | Gray et al. | |
| 6,382,923 B1 | 5/2002 | Gray | |
| 6,383,158 B1 | 5/2002 | Utterberg et al. | |
| 6,406,276 B1 | 6/2002 | Normand et al. | |
| 6,409,696 B1 | 6/2002 | Toavs et al. | |
| 6,416,293 B1 | 7/2002 | Bouchard et al. | |
| 6,459,175 B1 | 10/2002 | Potega | |
| 6,464,878 B2 * | 10/2002 | Utterberg | 210/645 |
| 6,468,424 B1 | 10/2002 | Dönig et al. | |
| 6,497,674 B1 | 12/2002 | Steele et al. | |
| 6,497,676 B1 | 12/2002 | Childers et al. | |
| 6,503,062 B1 | 1/2003 | Gray et al. | |
| 6,514,225 B1 | 2/2003 | Utterberg et al. | |
| 6,520,747 B2 | 2/2003 | Gray et al. | |
| 6,536,278 B1 | 3/2003 | Scagliarini | |
| 6,558,343 B1 | 5/2003 | Neftel | |
| 6,592,542 B2 | 7/2003 | Childers et al. | |
| 6,595,944 B2 | 7/2003 | Balschat et al. | |
| 6,604,908 B1 | 8/2003 | Bryant et al. | |
| 6,614,008 B2 | 9/2003 | Tidrick | |
| 6,648,845 B1 | 11/2003 | Gotch et al. | |
| 6,663,359 B2 | 12/2003 | Gray | |
| 6,685,831 B2 | 2/2004 | Dönig et al. | |
| 6,702,774 B1 | 3/2004 | Polaschegg | |
| 6,709,417 B1 | 3/2004 | Houle et al. | |
| 6,725,726 B1 | 4/2004 | Adolfs et al. | |
| 6,726,656 B2 | 4/2004 | Kamen et al. | |
| 6,730,055 B2 | 5/2004 | Bainbridge et al. | |
| 6,746,514 B2 | 6/2004 | Bedingfield et al. | |
| 6,749,403 B2 | 6/2004 | Bryant et al. | |
| 6,755,801 B2 | 6/2004 | Utterberg et al. | |
| 6,764,460 B2 | 7/2004 | Dolecek et al. | |
| 6,764,761 B2 | 7/2004 | Eu et al. | |
| 6,770,049 B2 * | 8/2004 | Ludt et al. | 604/6.16 |
| 6,790,195 B2 | 9/2004 | Steele et al. | |
| 6,808,369 B2 | 10/2004 | Gray et al. | |
| 6,814,547 B2 | 11/2004 | Childers et al. | |
| 6,852,090 B2 | 2/2005 | Burbank et al. | |
| 6,860,866 B1 | 3/2005 | Graf et al. | |
| 6,869,538 B2 | 3/2005 | Yu et al. | |
| 6,887,214 B1 | 5/2005 | Levin et al. | |
| 6,911,007 B2 | 6/2005 | Nier et al. | |
| 7,021,148 B2 | 4/2006 | Kuhn et al. | |
| 7,115,107 B2 | 10/2006 | Delnevo et al. | |
| 7,387,734 B2 | 6/2008 | Felding | |
| 7,517,387 B2 | 4/2009 | Chevallet et al. | |
| 2002/0000793 A1 | 1/2002 | Hanaki | |
| 2002/0017489 A1 | 2/2002 | Utterberg | |
| 2002/0072718 A1 | 6/2002 | Brugger et al. | |
| 2002/0107474 A1 | 8/2002 | Noack | |
| 2002/0147423 A1 | 10/2002 | Burbank et al. | |
| 2003/0018395 A1 | 1/2003 | Crnkovich et al. | |
| 2003/0029451 A1 | 2/2003 | Blair et al. | |
| 2003/0085621 A1 | 5/2003 | Potega | |
| 2003/0111457 A1 | 6/2003 | Tidrick | |
| 2003/0130606 A1 | 7/2003 | Tuck | |

| | | |
|---|---|---|
| 2003/0136189 A1 | 7/2003 | Lauman et al. |
| 2003/0200812 A1 | 10/2003 | Kuhn et al. |
| 2003/0204162 A1 | 10/2003 | Childers et al. |
| 2003/0217957 A1 | 11/2003 | Bowman et al. |
| 2003/0217961 A1 | 11/2003 | Hopping |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0220608 A1 | 11/2003 | Huitt et al. |
| 2003/0220609 A1 | 11/2003 | Childers et al. |
| 2003/0220627 A1 | 11/2003 | Distler et al. |
| 2004/0010223 A1 | 1/2004 | Busby et al. |
| 2004/0019312 A1 | 1/2004 | Childers et al. |
| 2004/0019313 A1 | 1/2004 | Childers et al. |
| 2004/0019320 A1 | 1/2004 | Childers et al. |
| 2004/0031756 A1 | 2/2004 | Suzuki et al. |
| 2004/0064080 A1 | 4/2004 | Cruz et al. |
| 2004/0067161 A1 | 4/2004 | Axelsson |
| 2004/0082903 A1 | 4/2004 | Micheli |
| 2004/0122353 A1 | 6/2004 | Shahmirian et al. |
| 2004/0135078 A1 | 7/2004 | Mandro et al. |
| 2004/0195190 A1 | 10/2004 | Min et al. |
| 2005/0054968 A1 | 3/2005 | Giannella |
| 2005/0126998 A1 | 6/2005 | Childers |
| 2005/0151422 A1 | 7/2005 | Gilmour |
| 2005/0230292 A1 | 10/2005 | Beden et al. |
| 2005/0234381 A1 | 10/2005 | Niemetzer et al. |
| 2005/0242034 A1 | 11/2005 | Connell et al. |
| 2006/0195064 A1 | 8/2006 | Plahey et al. |
| 2007/0106198 A1 | 5/2007 | Folden et al. |
| 2007/0193940 A1 | 8/2007 | Duchamp et al. |
| 2007/0269340 A1 | 11/2007 | Dannenmaier et al. |
| 2009/0071911 A1 | 3/2009 | Folden et al. |

FOREIGN PATENT DOCUMENTS

| | | |
|---|---|---|
| EP | 0311848 | 4/1989 |
| EP | 0 327 136 | 8/1989 |
| EP | 0 728 509 | 8/1996 |
| EP | 1529545 | 5/2005 |
| EP | 1277485 | 11/2006 |
| WO | WO 92/11046 | 7/1992 |
| WO | WO 96/25214 | 8/1996 |
| WO | WO 96/40320 | 12/1996 |
| WO | WO 03/043680 | 5/2003 |
| WO | WO 2007/050211 | 5/2007 |

OTHER PUBLICATIONS

U.S. Appl. No. 12/388,003, entitled Extracorporeal Fluid Circuit and Related Components, filed Feb. 18, 2009.

Gambro®, "DEHP-Free Cartridge Blood Sets", © Nov. 2004, Gambro, Inc, Lakewood, CO, 4 pp.

Gambro®, Prisma® HF 1000, "For Increased Filtration Capacity", © Aug. 2001, Gambro Renal Products, Inc., Lakewood, CO, 2 pp.

Impact of sodium and ultrafiltration profiling on haemodialysis-related hypotension, NDT Advance Access published online on Sep. 5, 2006, Yi Lun Zhou, Hui Lan Liu, Xiao Feng Duan, Ying Yao, Yi Sun, and Qun Liu.

Kidney International, vol. 66 (2004), pp. 1232-1238, Clinical consequences of an individualized dialysate sodium prescription in hemodialysis patients, Flavio M. DePaula, Aldo J. Peixoto, Luciano V. Pinto, David Dorigo, Pedro J.M. Patricio, and Sergrio F.F. Santos, Dec. 2004.

Kidney International, vol. 66, Supplement 89 (2004), pp. S1-S22, Mechanisms determining the ratio of conductivity clearance to urea clearance, Frank A. Gotch, Froilan M. Panlilio, Rosemary A. Buyaki, Erjun X. Wang, Thomas I Folden, and Nathan W. Levin.

Sleep Safe™ Operating Instructions, Fresenius Medical Care, Aug. 2000.

U.S. Appl. No. 29/224,370, filed Feb. 28, 2005, and entitled "Peritoneal Dialysis Cycler".

U.S. Appl. No. 29/224,371, filed Feb. 28, 2005, and entitled "Cassette for Peritoneal Dialysis Cycler".

U.S. Appl. No. 29/224,375, filed Feb. 28, 2005, and entitled "Peritoneal Dialysis Cycler".

Gambro®, "DEHP-free cartridge blood sets," © Nov. 2004, Gambro, Inc., Lakewood, CO, 4 pp.

Instructions for Optiflux F200NR F180N F160NR Hollow Fiber Dialyzers Not for Reuse, 89-711-58 Rev 10/04; Publication date Oct. 2004.

Gambro®, "Prisma® M60 and M100 Pre-Pump Infusion Sets—Introducing: The unique solution that enables Physicians to choose a predilution method that meets the needs of their patients", © Jan. 2004, Gambro Inc., Lakewood, CO, 4 pp.

Gambro®, "Prismaflex™, Anticipating Critical Care needs and taking our innovative response . . . to new heights", Jan. 2004, Gambro Inc., Lakewood, CO, 8 pp.

Manns, Markus et al., "The acu-men: A new device for continuous renal replacement therapy in acute renal failure," Kidney International, vol. 54, pp. 268-274, Feb. 1998.

Manus, Markus et al., "The acu-men: A new device for continuous renal repalcement therapy in acute renal failure," *Kidney International*, vol. 54, pp. 268-274, 1998.

Gambro®, "Prismaflex™ anticipating critical care needs and taking our innovative response . . . to new heights," © 2004, Gambro Inc., Lakewood, CO, 8 pp.

* cited by examiner

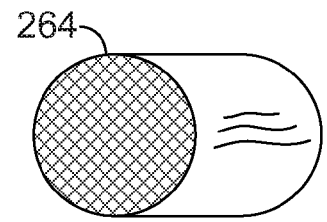
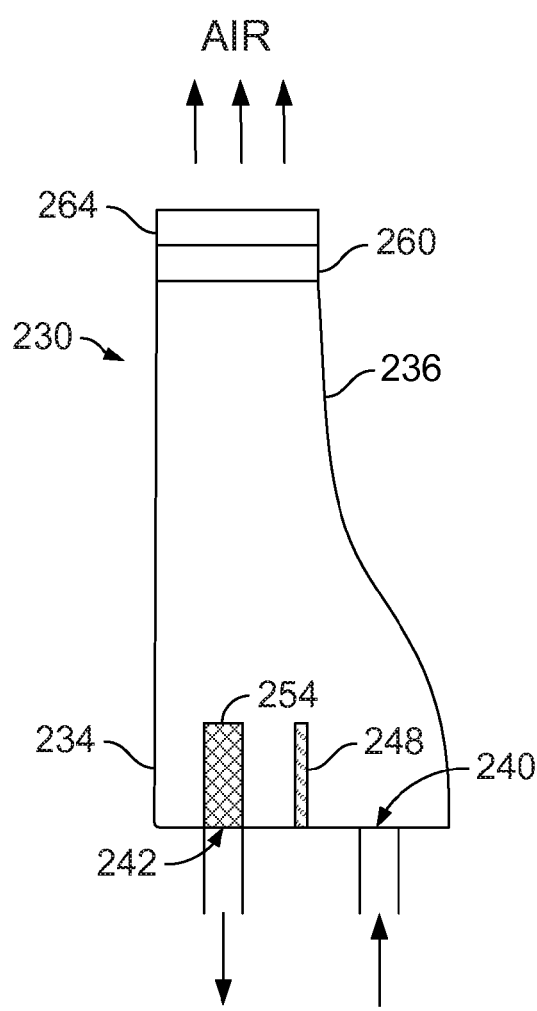
FIG. 3
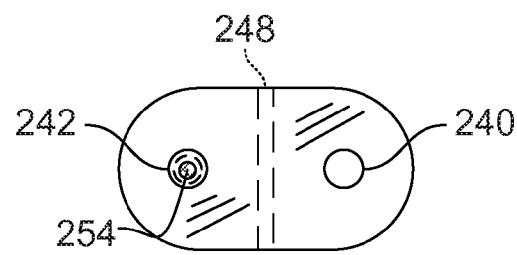
FIG. 3A
FIG. 3B
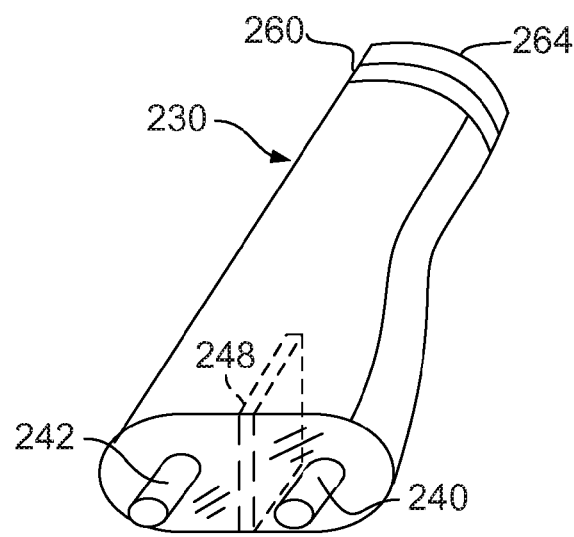
FIG. 3C

AUTOMATIC PRIME OF AN EXTRACORPOREAL BLOOD CIRCUIT

BACKGROUND

This invention relates to extracorporeal liquid circuits. Hemodialysis removes toxic substances and metabolic wastes from the bloodstream using an extracorporeal circuit with components designed to perform ultrafiltration and diffusion on the blood. Before the blood is returned to the body, air bubbles are removed from the blood to prevent embolisms.

Referring to FIG. 1, a typical extracorporeal circuit 100 includes tubing through which the blood flows and components for filtering and performing dialysis on the blood. Blood flows from a patient 105 through arterial tubing 110. Blood drips into a drip chamber 115 where a connecting tube from the drip chamber 115 attaches to a sensor 125 on a hemodialysis machine that determines the pressure of the blood on the arterial side of the circuit 100. A pump 120 forces the blood to continue along the path through the circuit 100. A dialyzer 130 separates waste products from the blood.

After passing through the dialyzer 130, the blood flows through venous tubing 140 into a second drip chamber 150. The drip chamber 150 can function as an air trap. Free gases in the blood may be able to escape into the drip chamber 150 before the blood continues to the patient. A sensor 170 is in communication with air in the drip chamber through tube 165. The sensor 170 can determine the pressure on the venous side of the circuit 100.

Heparin or drugs 160 can be added to the blood in the drip chamber 115. When blood is exposed to oxygen, the blood begins to clot. The drip chamber 150 may include a filter for preventing any clots from exiting the drip chamber 150 and entering the patient 105. The blood continues from the drip chamber through venous tubing 180 and through a bubble detector 175 before returning to the patient 105.

In addition to preventing clotting, air needs to be kept out of the venous line to prevent injecting air into the patient during treatment, which could result into air embolism.

SUMMARY

In one embodiment, a method of priming an extracorporeal blood circuit including a venous line, an arterial line and a line to a prime waste container, wherein any two of the venous line, arterial line and line to the waste container can be selectively in fluid communication with each other and a chamber including a filter that allows air to escape from the chamber is described. One of the venous line or the arterial line is occluded while connecting the other of the venous or arterial line to the prime waste container. Priming fluid is flowed through the circuit so that the priming fluid flows out of either the arterial or venous line into the waste container. The line to the waste container and connecting the arterial and venous lines together is occluded. Priming fluid is circulated through the closed extracorporeal circuit. The flow through the circuit is reversed, whereby air is removed from the circuit. The steps of occluding one of the venous line or the arterial line, flowing priming fluid, occluding the line to the waste container, circulating priming fluid and reversing the flow through the circuit are done without need for human manipulation.

In yet another embodiment, a method of priming an extracorporeal circuit including a venous line, an arterial line and a chamber with a filter that allows air to escape from the chamber while preventing liquid from escaping from the chamber is described. The method includes flowing fluid through the circuit in a forward direction and a backward direction, while the arterial line and the venous line define the circuit and a supply of priming solution is in line with the circuit, wherein flowing the fluid forces air out through the filter. The flowing is stopped after a quantity of fluid sufficient to fill the circuit completely has been released into the circuit and circulated and there is no longer air in the circuit.

In yet another embodiment, a hemodialysis system is described that is configured to be automatically primed. The system includes a prime fluid source container, a waste prime fluid container, an extracorporeal circuit and a clamping system. The extracorporeal circuit includes a venous line, an arterial line and a chamber including a filter that allows air to escape from the chamber. The prime fluid source container is in fluid communication with the arterial line, a three way connector connecting the venous line, the arterial line and a waste prime fluid container. The clamping system is configured to clamp the arterial line or a connection to the waste prime fluid container closed.

In another embodiment, a computer program product is described. The product is encoded on a computer-readable medium, operable to cause data processing apparatus to perform operations that control a hemodialysis machine. The operations include receiving instructions to initiate a priming sequence; in response to receiving the instructions, sending instructions to a clamping mechanism to cause the clamping mechanism to occlude a connection between a tube to a prime container and a first patient line; after the first patient line is occluded, sending instructions to a pump to cause the pump to run in a first direction to circulate fluid through a circuit for a first pumping time; determining when the first pumping time has elapsed; after determining that the first pumping time has elapsed, sending instructions to the clamping mechanism to open the first patient line, to cause the tube to the prime container to be occluded and to cause a second patient line to be no longer in fluid connection with the prime container and to only be in fluid connection with the first patient line; after the first patient line is connected to the second patient line, sending instructions to the pump to cause the pump to run in reverse.

Embodiments of the systems, methods and products may include one or more of the following features. Flowing priming fluid through the circuit may force air in the circuit out of the filter associated with the chamber. The direction of flow of the priming fluid can be reversed in the circuit multiple times, wherein reversing the direction of flow is programmed to be done automatically. An end of the arterial line can be disconnected and connecting the end of the arterial line to a patient. After connecting the arterial line to a patient, blood can be flowed from the patient into the circuit, wherein the circuit is air-free. A connection can be maintained between the waste container and the venous line while flowing blood from the patient into the circuit. A connection to the prime container can be clamped closed after the blood enters the venous line, the venous line can be connected from the line to the waste container and the venous line can be connected to the patient. A connection between the waste container and the venous line can be maintained while flowing blood from the patient into the circuit. An end of the venous line can be disconnected when the end of the arterial line is disconnected and the end of the venous line can be connected to the patient when the end of the arterial line is connected to the patient. Priming fluid can be flowed through the circuit to force air in the circuit out of a filter associated with a chamber in the circuit and the circulating can be stopped once air in the circuit has been eradicated from the circuit to form the air-free circuit. The circuit can include a dialyzer. Flowing priming fluid through the circuit, reversing the flow through the circuit and forcing air out of the circuit with the fluid define a priming sequence, and the method does not include inverting the dialyzer during any steps of the priming sequence. The arterial line can be occluded prior to flowing the fluid through the circuit and the arterial line can be opened after flowing the fluid through the circuit in a forward direction, but before flowing the fluid through the circuit in a backward direction. A connection to a prime container connected to the circuit can be opened contemporaneous with occluding the arterial line and the connection to the prime container can be occluded prior to flowing the fluid in the circuit in a backward direction contemporaneous with opening a connection to the arterial line.

A system can include a reversible pump for pumping fluid through the circuit and a controller configured to control the pump and to control the clamping system. The clamping system can include a two way clamp configured to alternatively clamp the arterial line or the connection to the waste prime fluid container closed. The system can include a holder for supporting the extracorporeal circuit and a dialyzer, wherein the dialyzer is non-rotatably secured to the holder. The clamping mechanism can include valves and/or a clamp.

A computer product can cause the data processing apparatus to perform operations including determining a pump reversal time, wherein sending instructions to the pump to cause the pump to run in reverse occurs at the pump reversal time. Determining a pump reversal time can include receiving an actual flow rate and determining the pump reversal rate from the actual flow rate and a predetermined forward pumping volume. The data processing operations can include receiving instructions to begin pumping fluid from a patient, in response to receiving the instructions to begin pumping fluid from a patient, sending instructions to the pump to run the pump and sending instructions to the clamping mechanism to open a connection between the second patient line and the prime container. The operations can include receiving instructions to stop the pump after opening the connection between the second patient line and the prime container and sending instructions to the pump to stop the pump in response to the instructions to stop the pump.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 is a schematic of an airless chamber.

FIG. 3A is a top view of the airless chamber.

FIG. 3B is a bottom view of the airless chamber.

FIG. 3C is a perspective bottom and side view of the airless chamber.

Like reference symbols in the various drawings indicate like elements.

DETAILED DESCRIPTION

An extracorporeal blood circuit is described that includes a reversible pump for pumping fluid, i.e., priming fluid and blood, through the circuit, a venous line and an arterial line for connecting to a patient, a prime waste line for receiving waste prime solution prior to connecting the circuit to the patent and a coupler for connecting the lines together. The coupler, in combination with the reversible pump, allows for flexibility in priming the circuit. Priming solution can be flowed through the circuit in either direction to fill both the venous line and the arterial line and allow the priming solution to flow into the waste bag. In some embodiments, a waste bag is not used, but rather simply a container for capturing spent fluid, such as priming fluid and dialysate. For simplicity, a waste bag is referred to throughout the specification. Also, the arterial and venous lines can be connected together to form a closed circuit and the fluid in the circuit can be recirculated in the forward and backward directions.

Figure 1:
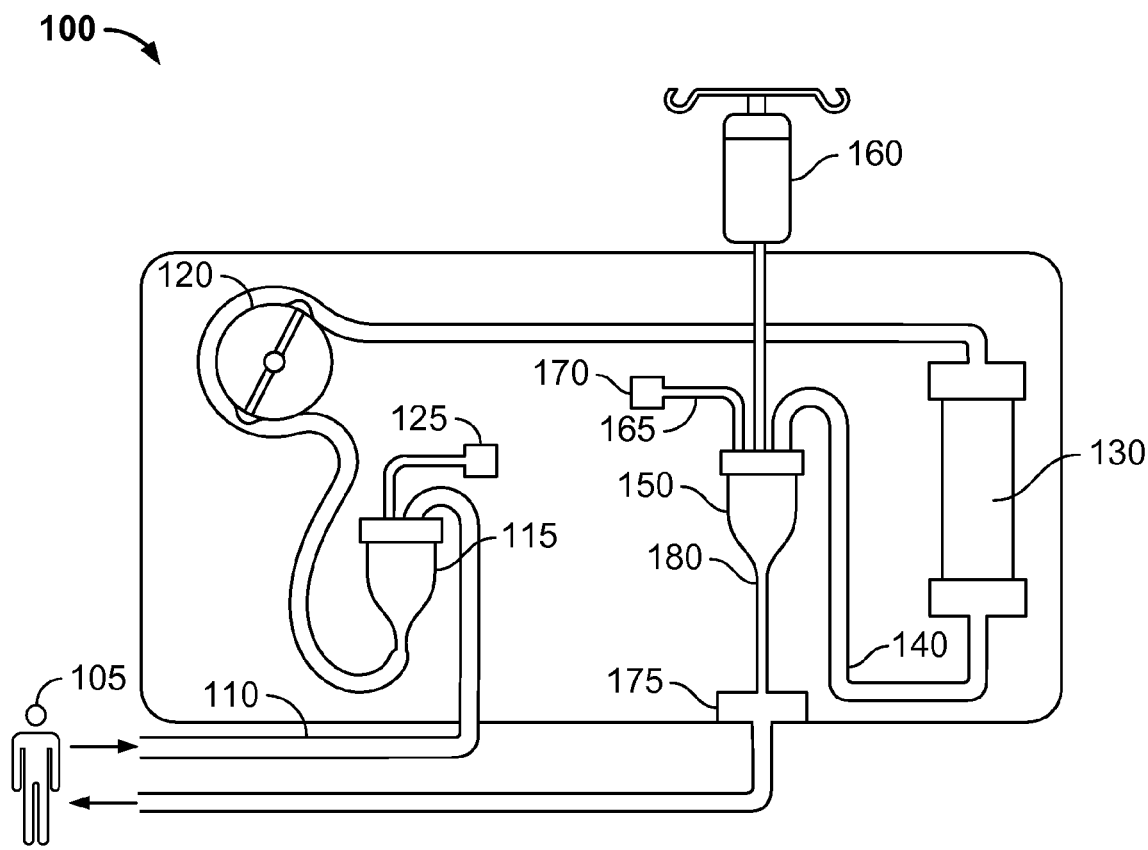
FIG. 1 is a schematic of a conventional hemodialysis system.
Figure 2:
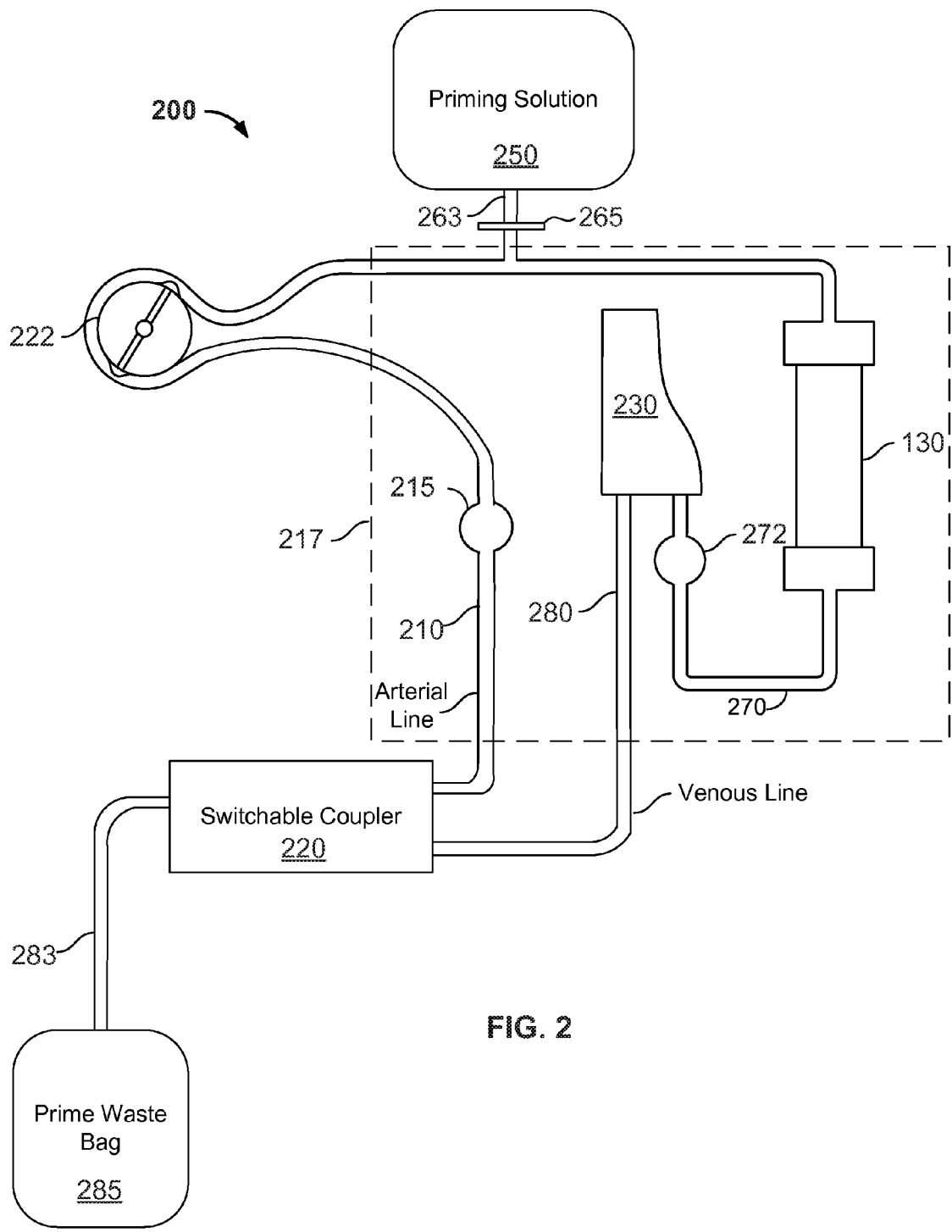
FIG. 2 is a schematic of the mechanical components of an autopriming hemodialysis system.

Referring to FIG. 2, an extracorporeal fluid circuit 200 includes components that allow for automatic priming of the system. A reversible pump 222, such as a peristaltic pump, is configured to force liquid through an arterial line 210 and venous line 280 in two directions, both forward and backward. Optionally, a sensor 215 is in line with the arterial line 210 to sense fluid pressure through the arterial line 210. The sensor 215 can include a transducer. In some implementations, the sensor 215 is after the reversible pump 222 on the arterial line 210, rather than before. A supply of saline 250, or other biocompatible fluid, such as dialysate, is connected to the arterial line, such as with a solution spike connector. A saline connection clamp 265 allows for a saline line 263 leading to the saline 250 to be occluded, thereby stopping the flow of saline into the circuit 200. In some embodiments, the saline is replaced with infusate solution. The arterial line 210 leads to a dialyzer 130 after pump 222. A dialyzer exit line 270 connects the dialyzer 270 to an airless chamber 230.

Referring to FIGS. 3, 3A, 3B and 3C, the airless chamber 230 includes is substantially hollow for filling with a liquid. The chamber 230 can be used for removing gas from blood, but can also be used with a number of other fluids, such as bodily fluids, including plasma or any extracorporeal blood/fluid processing procedure. The chamber 230 has a bottom region 234 and a top region 236, where the bottom and top are relative to the chamber's orientation during use. An entry port 240 and an exit port 242 are in the bottom region 234 of the chamber 230. In some implementations, the ports 240, 242 are located in a bottom surface of the chamber 230. In other implementations, at least one of the ports 240, 242 is located in a side surface of the chamber 230. In one implementation, a dam 248 is between the ports 240, 242. The optional dam 248 extends at least part way from one side wall to an opposite side wall. In one implementation, the dam 268 contacts each side wall so that all fluid entering entry port 240 flows over the top of the dam 248 before flowing out the exit port 242. In one implementation, a clot filter 254 is positioned adjacent to the exit port 242. Fluid flows through the clot filter 254 prior to flowing out of the exit port 242. In one implementation, the clot filter 245 has a pore size of between about 50-500 microns.

The ports 240, 242 are holes in the chamber which can be in fluid communication with tubular shaped extensions. The extensions are able to be connected to tubes, such as by pressure fitting or bonding. The extensions can be integrally formed with the chamber or subsequently attached to the chamber, such as by bonding or welding.

At the top region 236 of the chamber 230 is a microporous filter 260 and, optionally, a safety vent structure 264. The safety vent structure 264 may provide reduced condensation or minimize condensation on the microporous filter 260. The microporous filter 260 allows gas to vent from the chamber 230. Pores in the filter 260 range from 0.10 to 1 micron and are small enough to keep foreign particles and organisms from entering the chamber 230 from the outside air. In some embodiments, the vent structure 264 has a pore size between about 15 and 45 microns.

In one implementation, the filter 260 includes a hydrophobic material. A hydrophobic microporous filter keeps liquid from leaking out of the chamber 230 when the chamber 230 is substantially filled with liquid. A suitable filter has a pore size equal to or less than 0.45 microns, such as about 0.22 microns or about 0.2 microns. The filter may be formed of polytetrafluoroethylene (PTFE) or any other suitable material. In some embodiments, the filter 260 is a fibrous carrier with a matted and woven layer on top of which PTFE or other microporous material is applied. The hydrophobic microporous filter keeps liquid from leaking out of the chamber 230 when the chamber 230 is substantially filled with liquid and allows air to pass through. A suitable filter has a pore size equal to or less than 0.45 microns, such as between about 0.05 and 10 microns, for example about 0.22 microns or about 0.2 microns. Suitable filters are available from Pall Corporation, East Hills, N.Y., under the Versapor® mark and from W. L. Gore & Associates, Inc., Newark, Del.

The safety vent structure 264 is solid porous piece that allows air that escapes from the chamber to pass through. The vent structure 264 is self-sealing. When the vent structure 264 comes into contact with liquid, e.g., humidity or moisture, the material that forms the vent structure expands, or swells thereby closing off the pores. In some embodiments, the vent structure is formed of a blend of polyethylene and carboxymethylcellulose, a blend of polystyrene and methyl-ethyl-cellulose or of polypropylene- or polyethylene-based porous material. Such materials are available from Porex Corporation, Fairburn, Ga., such as EXP-816, which is a product containing 90% polyethylene and 10% carboxymethylcellulose with a 30-40 micron pore size. However, other percentages of the materials can be used, as well as other materials and other pore sizes.

The vent structure 264 is adjacent to the filter 260 so that the filter 260 is between the vent structure 264 and the chamber 230. The vent structure 264 prevents condensation from accumulating on and contacting the filter 260. In some embodiments, the vent structure 264 directly contacts the filter 260. The vent structure can be substantially disc shaped or can be another shape that is compatible with a chamber on which the vent structure is mounted. In some embodiments, the vent structure is between about 0.5 and 10 mm thick.

The shape of the chamber is approximately elongate. In some implementations, such as those shown in FIG. 3, the bottom region 234 of the chamber 230, 230' is wider than the top region 236, such that the chamber 230, 230' has a quasi-conical shape or a flare at the bottom. In some implementations, the top and bottom dimensions of the chamber are approximately equal so that the chamber has a rectangular or cylindrical shape. The bottom region 234 can also be narrower than the top region 236. If the ports 240, 242 are in the bottom surface of the chamber, the bottom surface has a sufficiently large dimension to accommodate the ports 240, 242 as well as any tubes coupled to the ports for directing fluid into and out of the chamber. For example, if the tubing has an outer diameter of 6.25 mm, the bottom surface is at least 12.5 mm wide. The exact dimensions of the chamber 230 are unimportant, although the chamber 230 can be at least about two inches in height, preferably three to four inches. The airless chamber 230 is described further in U.S. application Ser. No. 11/256,627, filed Oct. 21, 2005, "Extracorporeal Fluid Circuit", published May 10, 2007, as U.S. Publication No. 2007-0106198, which is incorporated herein by reference.

Referring back to FIG. 2, a venous pressure sensor 272 can be located between the dialyzer 130 and the airless chamber 230. Because the reversible pump allows for fluid flow in both directions through the circuit, the dialyzer 130 does not need to be rotatably mounted on a holder. Fluid can be pushed through the dialyzer 130 from the bottom up or from the top down without needing to invert the dialyzer. The airless chamber 230 is connected to a venous line 280. The venous line 280, arterial line 210 and a prime waste bag 285 are then releasably connected to a coupler 220.

The coupler allows the arterial line 210, the venous line 280 and a prime waste line 283, i.e., the line to the prime waste bag 285, to be connected to one another in a variety of ways. The coupler 220 allows fluid in the circuit to be diverted either from the arterial line or the venous line to the prime waste bag 285. The arterial line 210 and venous line 280 can also be connected to one another to form a closed circuit, rather than to the prime waste bag 285. The reversible pump 222 allows for changing the direction of the flow through the circuit.

In some embodiments, the features within region 217 (in phantom) can be implemented in a cassette, as further described in U.S. Publication No. 2007-0106198.

Figure 4:
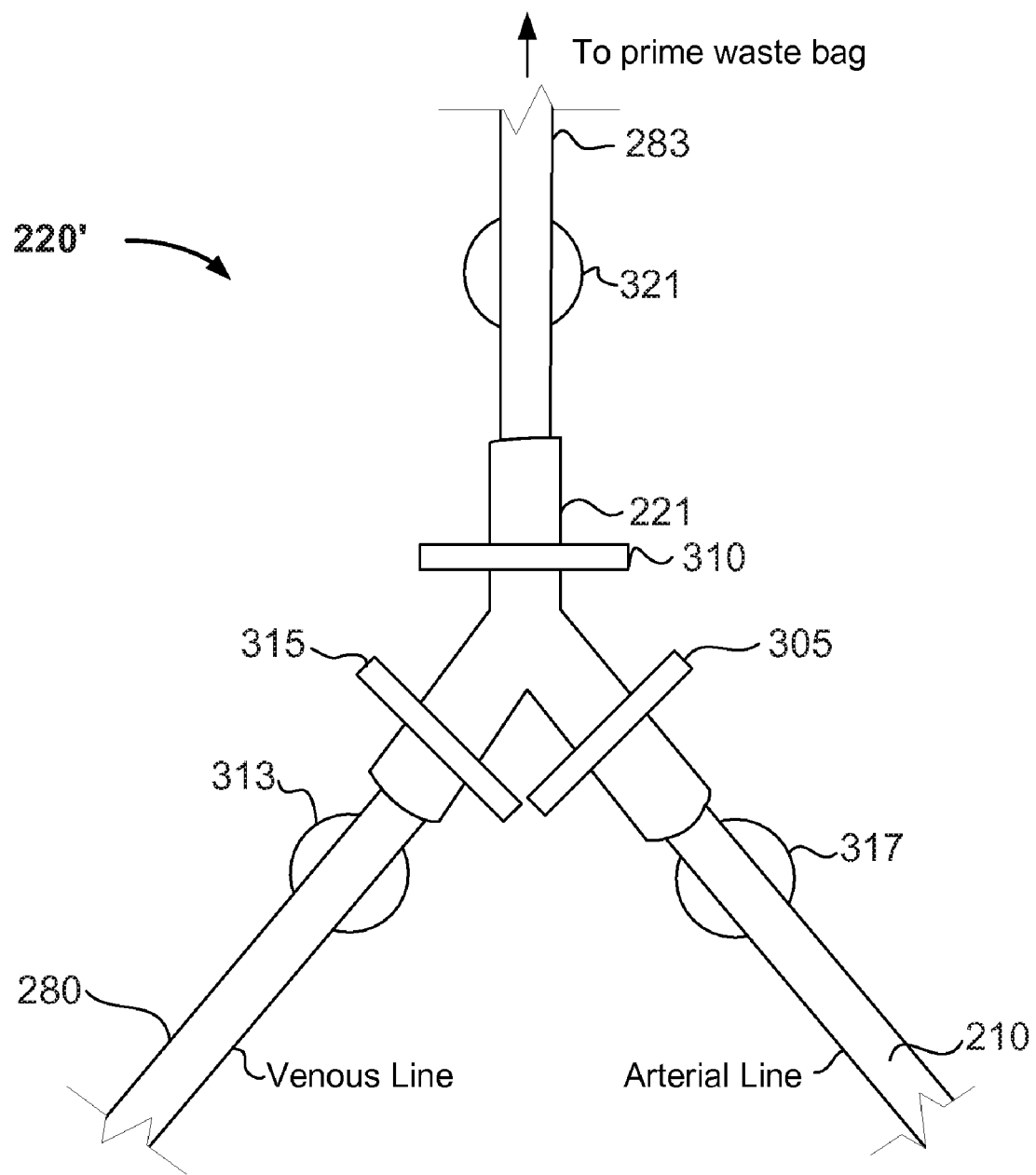
FIG. 4 is a schematic of connections between a prime bag, an arterial line and a venous line.

Referring to FIG. 4, the coupler 220' allows the venous line 280, arterial line 210 and prime waste bag 285 to be in fluid communication with each other. The prime waste bag 285 can include a prime waste line 283. In some embodiments, the coupler 220' includes a three-way Y-tube 221 with connectors (not shown) for connecting the Y-tube 221 to the lines. Suitable connectors include leur locks, quick connectors, threaded connectors and other suitable fittings for tubing. The coupler 220' also allows each of the venous line 280, arterial line 210 and prime waste line 283 to be individually sealed off from one another. The coupler 220' can include valves 305, 310, 315 or clamps that allow each line to be occluded. In some embodiments, the coupler 220' fits against a machine on which the tubing is mounted. The machine includes valves, such as bubble or balloon, solenoid or pneumatic valves, that when actuated expand and close off the tubing adjacent to the valve. The valves can be adjacent to the coupler 221. In some embodiments, instead of valves the coupler 220' includes mechanical clamps or occluder bars that press down on the Y-tube when a line is to be occluded. In addition, a valve 313, 317, 321 or clamp, such as pinch clamps, can be on each of the lines so that the lines can be disconnected from the coupler 220' without leaking. In some embodiments, a connector on each of the lines which mates the coupler 220' has a valve or other mechanism that automatically closes off the line when the line is disconnected from the Y-tube 221. That way, fluid leak is prevented when the lines are removed from the coupler 220'.

In some embodiments, the coupler 220' includes a door on a front of the machine that can be tightly closed to the front of the machine to enable the valves to place sufficient pressure on the Y-tube 221 or lines to occlude the connections between the lines. In some embodiments, the coupler 220' includes a switching valve instead of a Y-tube. The switching valve rotates to open up a connection between two lines at one time and simultaneously closes off a connection to the third line.

Figure 5A:
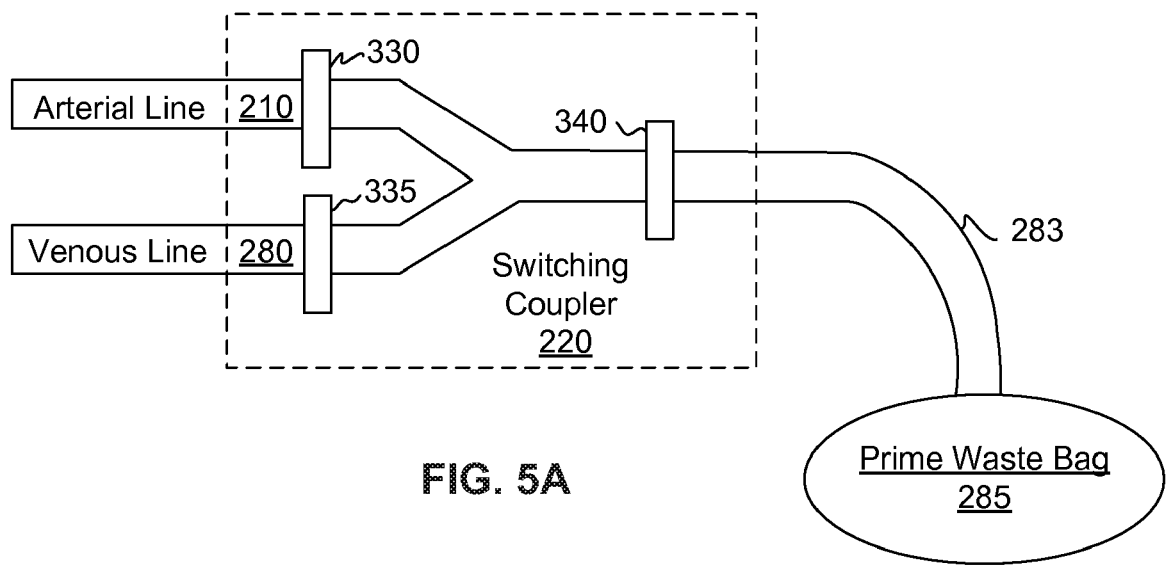
FIG. 5A is a schematic of a connection between a prime bag, an arterial line and a venous line.

Referring to FIG. 5A, a schematic diagram shows the coupler 220 with the arterial line 210, venous line 280 and the prime waste line 283 each with respective clamps 340, 335 and 330. When all of the clamps are open, or off, the lines 210, 280, 283 are all fluidly coupled to one another. However, engaging one of the clamps prevents fluid flow into or out of the respective line. The clamps can be implemented preferably as pneumatically actuated values that in effect pinch the lines closed, or pneumatic or solenoid operated clamps can be deployed. In some embodiments the clamps on two lines may be mechanically linked so that their operation is mutually exclusive, i.e., if one is open, the other is closed.

Figure 5B:
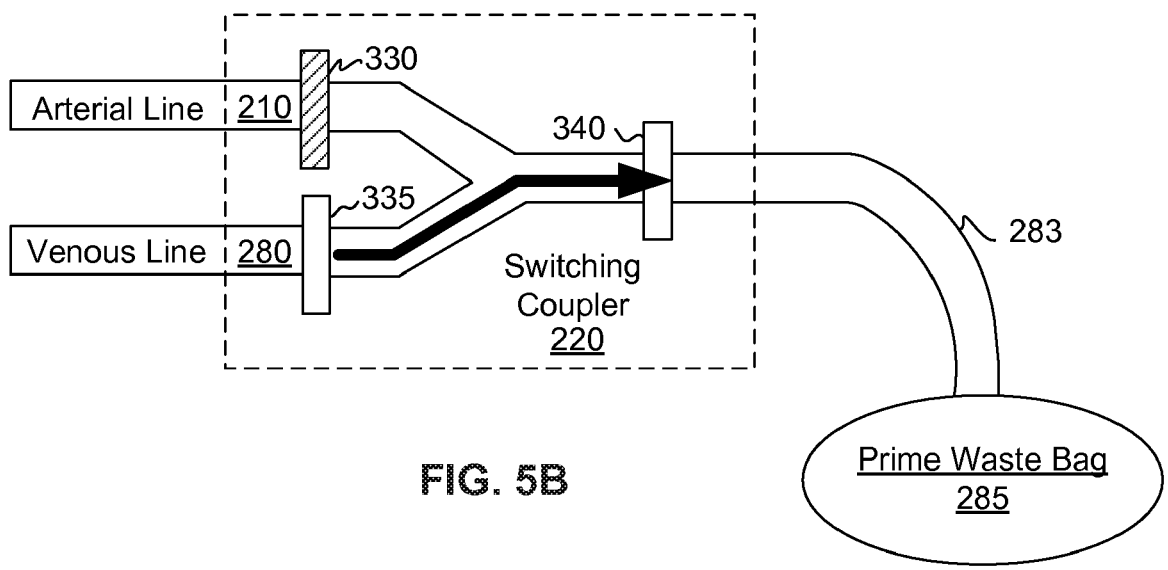
FIGS. 5B-5E show flow through the arterial line, venous line the line to the prime waste bag when the line are alternatively clamped or open.
Figure 5C:
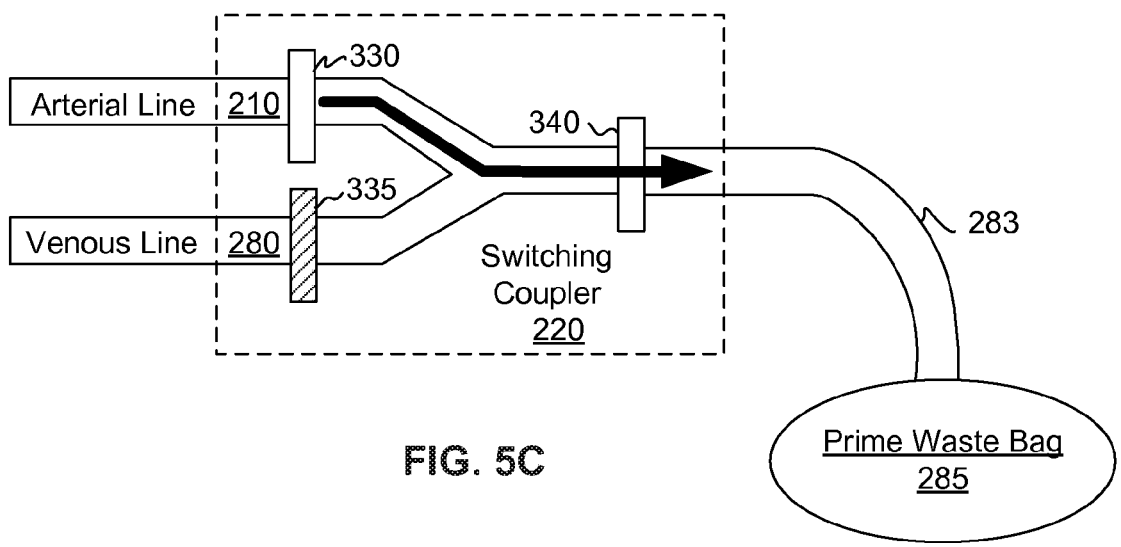
Figure 5D:
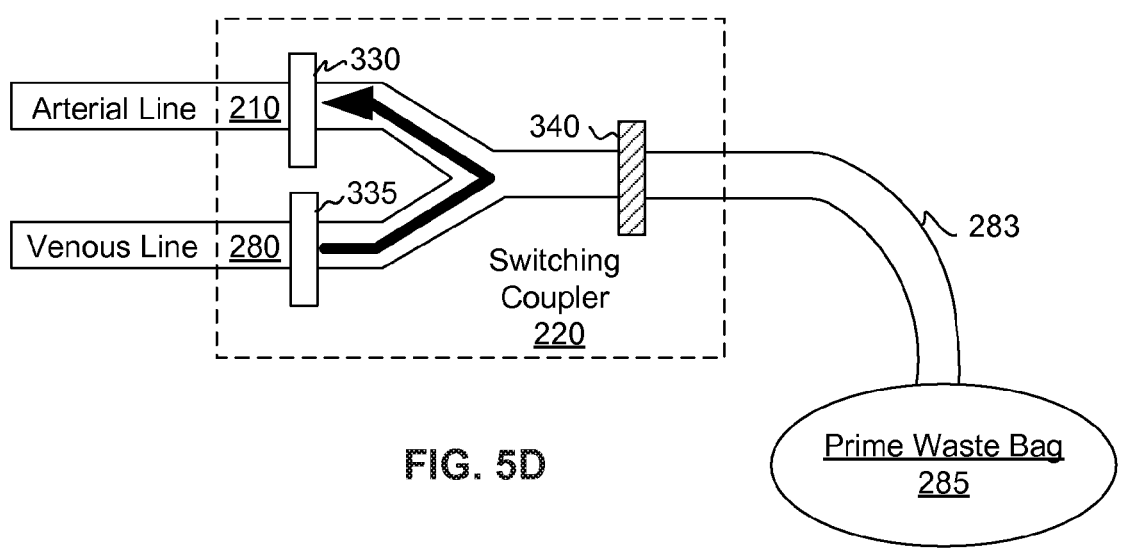
Figure 5E:
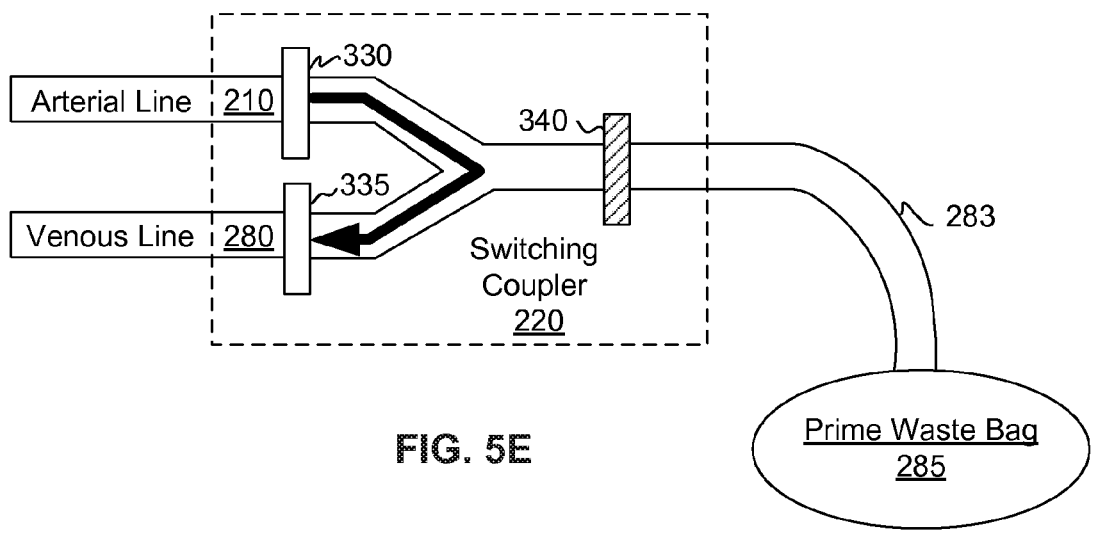

Referring to FIG. 5B, closing the clamp 330 on the arterial line 210 stops any fluid flow into or out of arterial line 210. This, in combination with running the pump in the forward direction, allows for fluid (indicated by the arrow) to be pumped from the venous line 280 into the prime waste bag 285. Referring to FIG. 5C, closing only the clamp 335 on the venous line 280 and reversing the pump direction allows fluid to flow, or be pumped, from the arterial line 210 into the prime waste bag 285. Referring to FIG. 5D, closing the clamp 340 on the line 283 to the waste prime bag 285 allows for forming a semi-closed circuit, where fluid can be circulated through the circuit without diverting any of the fluid to the waste prime bag 285. When the pump in the forward direction, fluid flows from the venous line 280 into the arterial line 210. Referring to FIG. 5E, by maintaining the clamp 340 on the prime line bag line 283 closed and reversing the pump direction, the flow can be reversed in the circuit, so that fluid flows from the arterial line 210 into the venous line 280. In some embodiments, the clamps are electronically controlled, or are automatic. In other embodiments, the clamps are manual controls, that is, the clamps are controlled by an operator.

Figure 6:
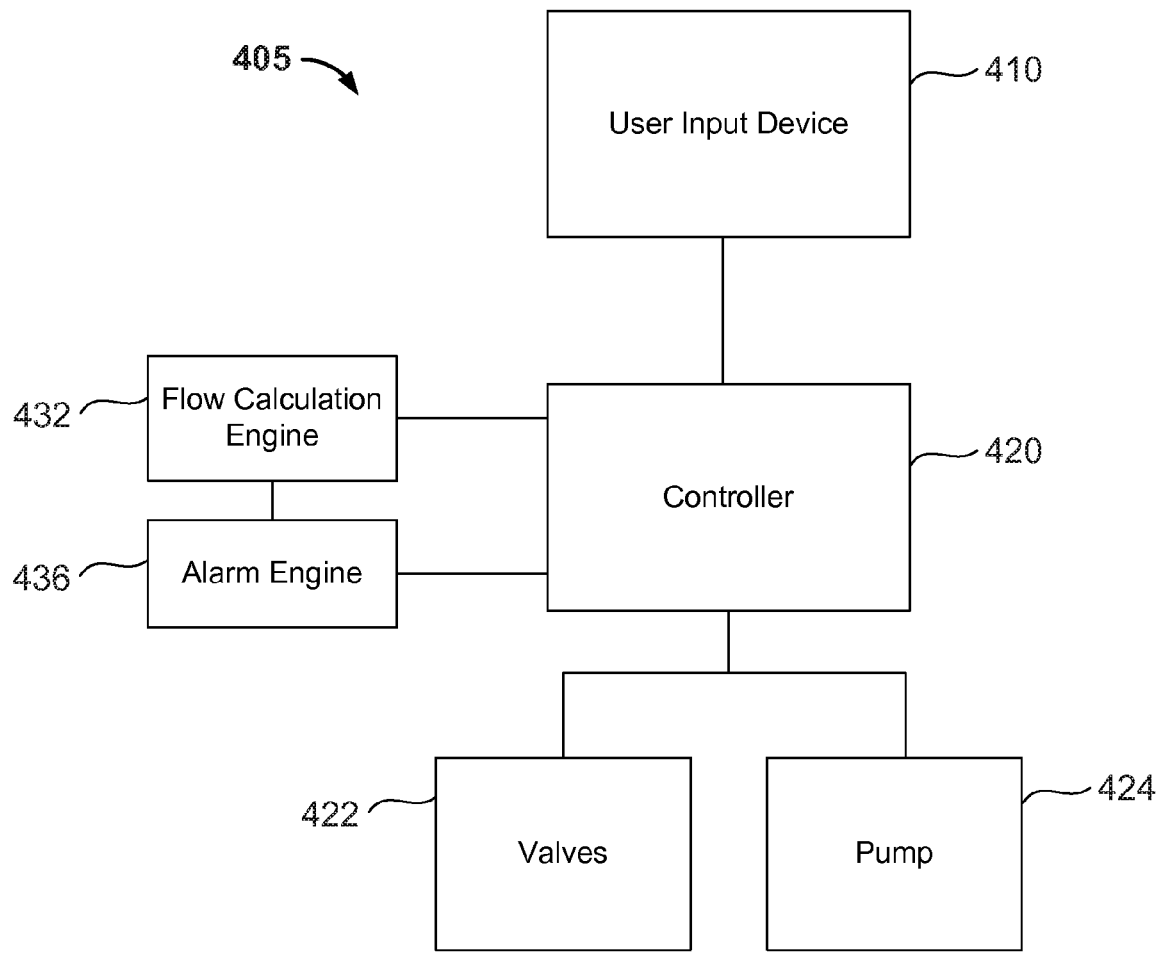
FIG. 6 is a schematic of a hemodialysis control system.

Referring to FIG. 6, the extracorporeal fluid circuit 200 is controlled by a computer system 405 that allows an operator to start and stop the priming sequence and runs the priming sequence steps automatically. The computer system 405 includes a user input device 410. The user input device 410 allows the operator to select a sequence, being running the sequence, select parameters for running a sequence, access menus and help information and stop the machine as required. One such programmed sequence is a priming sequence, as described further herein. The user input device can include a keyboard, buttons, a touch screen, a mouse or other suitable input device. The instructions an operator inputs to the computer system 405 using the input device 410 are relayed to a controller 420. The controller 420 is programmed or is in communication with instructions for controlling flow through the fluid circuit. In some embodiments, the fluid circuit is a series of disposable tubes, a chamber, a dialyzer, a cassette, such as described in the '627 application, or some combination of these elements that are connected to a machine having valves 422 and a pump 424. The controller 420 is able to control the direction of the pump and the starting and stopping of the pump. The controller 420 can also actuate the valves, or other occlusion devices, to cause the valves to seal off one or more tubes or lines. Optionally, the controller 420 is in communication with a flow calculation engine 432 that determines the flow rate from the blood pump. In some embodiments, the system 405 is programmed with both a control process and a safety process. The control process controls the priming functions, such as running the pump. The safety process monitors the machine while it is running, for example, the safety process can monitor the circuit for blood in the line. If blood is detected in the line, the safety process stops any priming sequence that is being run. The flow calculation engine 432 can communicate the flow rate to the controller 420, which in turn can increase or decrease the pump rate. The controller 420 can also be in communication with an alarm engine 436. If the flow rate is too high or low, the alarm engine 436 can sound an alarm to notify the operator and signal the controller to stop the pump or take other appropriate action.

Figure 7:
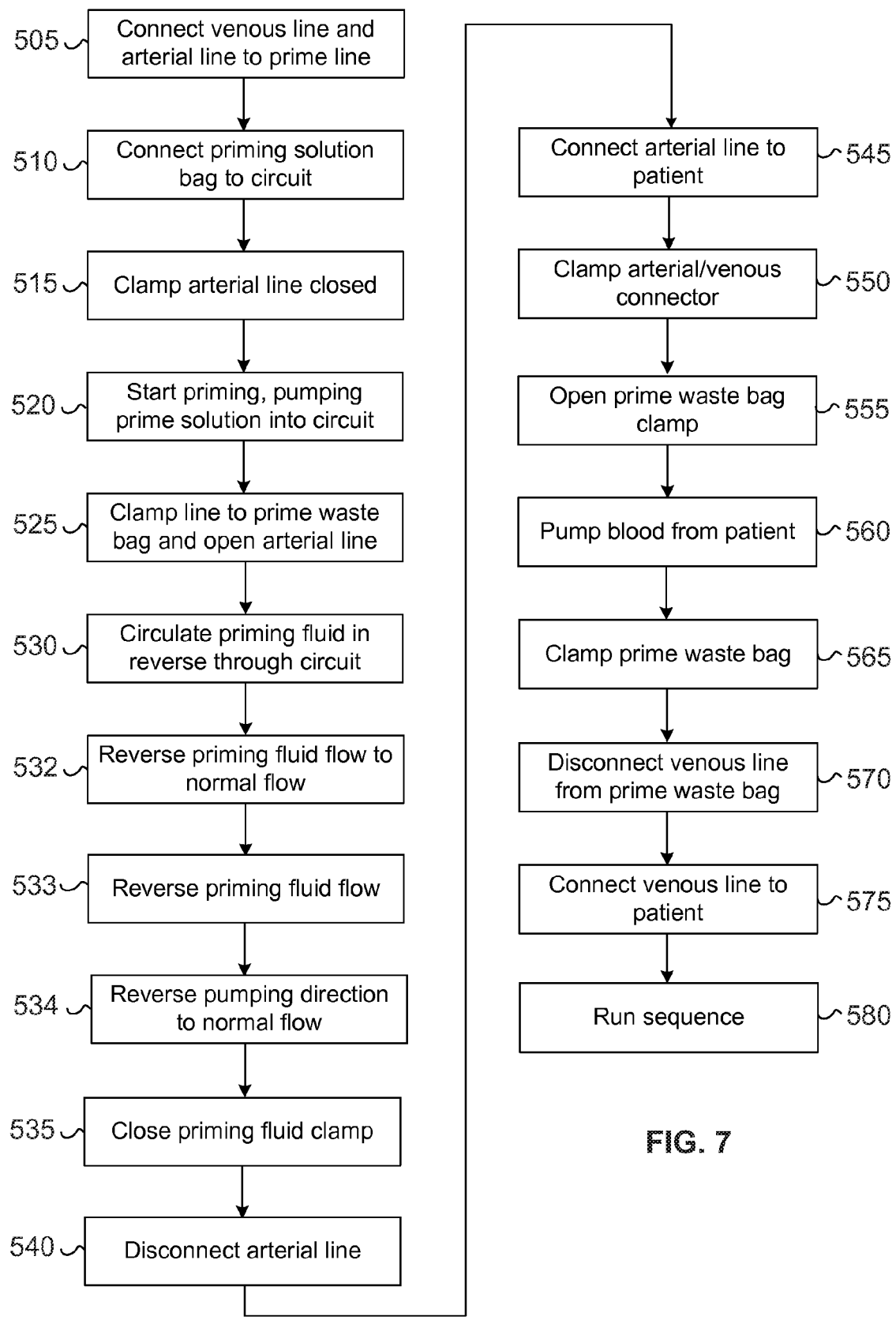
FIG. 7 is a flow chart describing use of the autopriming hemodialysis system.

Referring to FIG. 7, the coupler for causing the arterial, venous and prime waste bag line to be in selectable communication with one another in combination with the reversible pump and the airless chamber allow for autopriming of the circuit prior to connecting the arterial and venous lines to a patient. That is, the blood tubing circuit can be placed on a dialyzer machine and the machine can be instructed to prime the circuit automatically without any intervention from a human. An exemplary set of steps for priming the circuit follow. The circuit, including the venous line and the arterial line are connected to the prime waste bag (step 505). A priming solution, such as saline, is connected to the circuit, as to the arterial line while the saline bag is clamped closed (step 510). The arterial line is clamped closed (step 515). An operator instructs the machine to start a prime sequence, such as by selecting a "prime" button on an input panel. The prime sequence begins, pumping prime solution into circuit (step 520). Priming solution is pumped through the arterial line and through the dialyzer and the circuit. In some embodiments, a predetermined quantity of priming solution is pumped into the arterial line, such as 250 ml of solution. The volume of priming solution that is initially pumped into the circuit can be sufficient to fill the airless chamber. The volume of priming solution is measured by the pump stroke and calculated stroke volume. If the machine detects that no priming solution is being circulated through the circuit, such as if the saline bag is not attached or is clamped shut, the machine can alert the operator.

The line to the prime waste bag is clamped closed and the arterial line is opened (step 525). This allows the arterial line to form a complete circuit with the venous line through the coupler. After running the pump in the forward or normal direction, the pump circulates priming fluid through the circuit in the reverse direction (step 530). In some embodiments, the pump is run in the reverse direction at a rate of 200-300 ml/min for two minutes. The pump is again reversed (step 532), thereby pushing priming fluid in the normal direction and downstream of the connection of the priming fluid bag to the circuit. Filling the circuit with priming fluid with the prime waste bag connection occluded forces priming fluid through the line to the chamber. When priming fluid fills the bottom of the chamber from both the arterial and venous lines, continuing to flow the fluid through the circuit causes any air upstream of the pump to be pushed out of the top of the chamber, through the filter assembly. In some embodiments, the pump is run at a flow rate of 400-500 ml/minute for five minutes. The pump is stopped.

Because there can be additional air in the circuit upstream of the pump, the pump is again reversed and again circulates fluid through the circuit (step 533). In some embodiments, the flow rate is at 400 ml/min. The priming fluid is circulated for some minimum amount of time, such as two minutes, e.g., about five minutes. Any of the pump reversing steps are optional. In some embodiments, the priming fluid is simply flowed through the circuit in only one direction or the direction of flow is only reversed one or two times during priming. The flow rate can be increased or decreased to facilitate pushing air out of the dialyzer and venting the air through the filter. In some embodiments, one of the lines, such as the venous line, is clamped periodically while pumping fluid through the circuit to build up the pressure in the circuit. This essentially pushes fluid through the dialyzer to further force air out of the circuit.

In some methods, in addition to the priming fluid being used to push air out of the system, dialysate can also be used to push air out of the system. Dialysate is introduced into the dialyzer through a separate circuit from the blood circuit. The dialyzer has semi-permeable hollow membranes that allow liquid and small molecules to pass through. Dialysate that is introduced onto one side of membranes can permeate through to the other side of the membrane and assist in pushing air out of the system, while the priming fluid is running through the system, before or after.

After the priming fluid has been circulated through the circuit for a substantial length of time that all of the air has been vented from the circuit and that human intervention is not required to determine that all the air has been removed from the circuit through the hydrophobic filter, the pump stops and, if necessary, the pump reverses to the normal flow direction. In some embodiments, a level detector detects the level of liquid in the chamber. When the level detector detects that a sufficient level of liquid is in the chamber, the circuit is determined to have been sufficiently primed. The machine is then idle until the patient and operator are ready to connect the circuit to the patient. When the air is removed from the circuit, the pump direction is reversed, if necessary, to the normal flow direction (step 534).

The priming solution connection pump is closed, such as by clamping the line (step 535). The arterial line is disconnected from the coupler (step 540). The arterial line is connected to the patient (step 545). The connector between the arterial and venous connector is closed (step 550). The line to the prime waste bag is opened (step 555). In some embodiments, clamping the arterial line closed automatically opens the line to the prime waste bag. The operator initiates the next pumping sequence. Optionally, the operator selects a desired pumping rate, such as a rate determined by the patient's health, weight or body condition. The pump pumps blood from the patient (step 560), causing priming solution to move through the circuit and either into the prime waste bag or infused directly into the patient. When a predetermined quantity of priming solution has been pumped into the prime waste bag, or when the machine determines that the circuit is free of air, the pump is stopped and the connection to the prime waste bag is closed (step 565). The venous line is disconnected from the prime waste bag (step 570). The patient is then connected to the venous line (step 575). The prime waste bag can be discarded. Once the patient is connected to the venous line, the dialysis program is run (step 580). If the priming solution is a solution such as saline or other physiologically compatible fluid, some amount of priming solution in the venous line is acceptable to pump into the patient.

In an alternative embodiment of priming the system, both the arterial line and the venous line are disconnected from one another simultaneously and connected to the patient simultaneously. The priming sequence, that is, the pump, is stopped. The clamp to the prime waste bag is closed prior to disconnecting the venous and the arterial lines. The venous and arterial lines are disconnected from one another and connected to the patient. Because there is priming fluid in the venous lines, the patient receives priming fluid as blood begins to flow from the patient into the circuit. The excess fluid introduced into the patient can be removed by ultrafiltration during the hemodialysis treatment.

In some embodiments, a coupler with clamps is not required to prime the circuit. If the venous line and arterial line are connected to one another, the priming sequence can be run by allowing the priming solution to drain into the circuit. When the priming solution reaches the portion of the circuit that is adjacent to the pump, the pump can be run to push solution through the circuit. Because air is able to flow out the top of the chamber, the circuit continues to fill until all of the air space is filled with liquid. The pump can be reversed to cause the fluid to dislodge any air bubbles trapped in the circuit. Because the direction of flow is reversed in order to dislodge any air trapped in the system, air can be pushed through the system without the need for inverting the dialyzer during priming, as is required in some conventional dialyzer systems. Thus, the dialyzer system is able to automatically prime the circuit prior to being connected to a patient without intervention from a human.

Connecting the venous line and arterial line to an extracorporeal circuit with an airless chamber allows a user to automatically run a priming sequence and evacuate all of the air from the system. Because the system cycles priming fluid through the circuit in both directions a number of times and for a predetermined volume of fluid, the operator can be confident that all air has been removed from the system without having to visually inspect the circuit prior to connecting a patient to the system. This frees the operator, e.g., a technician, from manually priming the system. The operator can use the time that the system is being primed to prepare the patient or complete other tasks. Because the system runs a predetermined volume of fluid through the system and stops, the system is less likely to be run dry because of the operator forgetting to turn the priming step off. Because the priming sequence is run for a sufficient amount of time, the probability of any air in the circuit is very low. Any air that is in the circuit ought to escape through the chamber. This reduces the risk of embolism to the patient, thereby increasing the patient's safety when using the machine.

In embodiments, control of the functional operations described in this specification can be implemented in digital electronic circuitry, or in computer software, firmware, or hardware, including the structures disclosed in this specification and their structural equivalents, or in combinations of one or more of them. Embodiments of the control features can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., an LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

A number of embodiments have been described. Nevertheless, it will be understood that various modifications may be made without departing from the spirit and scope of the invention. Accordingly, other embodiments are within the scope of the following claims.

What is claimed is:

1. A method of priming an extracorporeal blood circuit including a venous line, an arterial line and a line to a prime waste container, wherein any two of the venous line, arterial line and line to the waste container can be selectively in fluid communication with each other, and a chamber including a filter that allows air to escape from the chamber, the method comprising:
   occluding one of the venous line or the arterial line while connecting the other of the venous or arterial line to the prime waste container;
   flowing priming fluid through the circuit so that the priming fluid flows out of either the arterial or venous line into the waste container;
   occluding the line to the waste container and connecting the arterial and venous lines together;
   circulating priming fluid through the closed extracorporeal circuit;
   reversing the flow through the circuit, whereby air is removed from the circuit; and
   detecting a liquid level in the chamber to determine whether the extracorporeal blood circuit has been sufficiently primed,
   wherein the steps of occluding one of the venous line or the arterial line, flowing priming fluid, occluding the line to the waste container, circulating priming fluid, reversing the flow through the circuit, and detecting the liquid level in the chamber are done without need for human manipulation, and
   wherein a liquid entry port and a liquid exit port are in a bottom region of the chamber, and the filter is in a top region of the chamber.

2. The method of claim 1, wherein flowing priming fluid through the circuit forces air in the circuit out of the filter associated with the chamber.

3. The method of claim 1, further comprising reversing direction of flow of the priming fluid in the circuit multiple times, wherein reversing the direction of flow is programmed to be done automatically.

4. The method of claim 1, further comprising:
   disconnecting an end of the arterial line; and
   connecting the end of the arterial line to a patient.

5. The method of claim 4, further comprising after connecting the arterial line to a patient, flowing blood from the patient into the circuit, wherein the circuit is air-free.

6. The method of claim 5, further comprising maintaining a connection between the waste container and the venous line while flowing blood from the patient into the circuit.

7. The method of claim 6, further comprising:
   clamping closed a connection to the prime container after the blood enters the venous line;
   disconnecting the venous line from the line to the waste container; and
   connecting the venous line to the patient.

8. The method of claim 7, wherein the venous line is disconnected from the line to the waste container after flowing blood from the patient into the circuit.

9. The method of claim 4, further comprising:
   disconnecting an end of the venous line when the end of the arterial line is disconnected; and
   connecting the end of the venous line to the patient when the end of the arterial line is connected to the patient.

10. The method of claim 1, further comprising:
    flowing priming fluid through the circuit to force air in the circuit out of the filter associated with a the chamber in the circuit; and
    stopping the circulating once air in the circuit has been eradicated from the circuit to form the air-free circuit.

11. The method of claim 1, wherein:
    the circuit includes a dialyzer;
    flowing priming fluid through the circuit, reversing the flow through the circuit and forcing air out of the circuit with the fluid define a priming sequence; and
    the method does not include inverting the dialyzer during any steps of the priming sequence.

12. The method of claim 1, wherein the filter is a hydrophobic microporous filter.

13. The method of claim 1, further comprising temporarily clamping the venous line while flowing the priming fluid through the circuit to build up pressure in the circuit.

14. The method of claim 1, wherein each of the arterial line, the venous line, and the line to the waste container is equipped with a clamp, and two of the clamps are mechanically linked so that their operation is mutually exclusive such that when one of the two clamps is open, the other of the two clamps is closed.

15. A method of priming an extracorporeal circuit including a venous line, an arterial line and a chamber with a filter that allows air to escape from the chamber while preventing liquid from escaping from the chamber, comprising:
    flowing fluid through the circuit in a forward direction and a backward direction, while the arterial line and the venous line define the circuit and a supply of priming solution is in line with the circuit, wherein flowing the fluid forces air out through the filter; and
    stopping the flowing after a quantity of fluid sufficient to fill the circuit completely has been released into the circuit and circulated and a level detector has detected a level of liquid in the chamber indicating that there is no longer air in the circuit, and wherein a liquid entry port and a liquid exit port are in a bottom region of the chamber, and the filter is in a top region of the chamber.

16. The method of claim 15, further comprising:
occluding the arterial line prior to flowing the fluid through the circuit; and
opening the arterial line after flowing the fluid through the circuit in a forward direction, but before flowing the fluid through the circuit in a backward direction.

17. The method of claim 16, further comprising:
opening a connection to a prime container connected to the circuit contemporaneous with occluding the arterial line; and
occluding the connection to the prime container prior to flowing the fluid in the circuit in a backward direction contemporaneous with opening a connection to the arterial line.

18. The method of claim 15, wherein the filter is a hydrophobic microporous filter.

19. The method of claim 15, further comprising temporarily clamping the venous line while flowing the fluid through the circuit to build up pressure in the circuit.

20. The method of claim 15, wherein each of the arterial line, the venous line, and the line to the waste container is equipped with a clamp, and two of the clamps are mechanically linked so that their operation is mutually exclusive such that when one of the two clamps is open, the other of the two clamps is closed.

21. A hemodialysis system configured to be automatically primed, comprising:
a prime fluid source container;
a waste prime fluid container;
an extracorporeal circuit including a venous line, an arterial line and a chamber including a filter that allows air to escape from the chamber, wherein a liquid entry port and a liquid exit port are in a bottom region of the chamber, and the filter is in a top region of the chamber, and the prime fluid source container is in fluid communication with the arterial line;
a three way connector connecting the venous line, the arterial line and a waste prime fluid container;
a clamping system configured to clamp the arterial line or a connection to the waste prime fluid container closed; and
a level detector configured to detect a level of liquid in the chamber for determining whether the extracorporeal circuit has been sufficiently primed.

22. The system of claim 21, further comprising:
a reversible pump for pumping fluid through the circuit; and
a controller configured to control the pump and to control the clamping system.

23. The system of claim 21, wherein the clamping system includes a two way clamp configured to alternatively clamp the arterial line or the connection to the waste prime fluid container closed.

24. The system of claim 21, wherein the clamping mechanism includes a plurality of valves.

25. The system of claim 21, wherein the clamping mechanism includes a clamp.

26. The system of claim 21, further comprising:
a holder for supporting the extracorporeal circuit; and
a dialyzer, wherein the dialyzer is non-rotatably secured to the holder.

27. The system of claim 21, wherein the filter is a hydrophobic microporous filter.

28. A computer program product, encoded on a computer-readable medium, operable to cause data processing apparatus to perform operations that control a hemodialysis machine comprising:
receiving instructions to initiate a priming sequence;
in response to receiving the instructions, sending instructions to a clamping mechanism to cause the clamping mechanism to occlude a connection between a tube to a prime container and a first patient line;
after the first patient line is occluded, sending instructions to a pump to cause the pump to run in a first direction to circulate fluid through a circuit for a first pumping time;
determining when the first pumping time has elapsed;
after determining that the first pumping time has elapsed, sending instructions to the clamping mechanism to open the first patient line, to cause the tube to the prime container to be occluded and to cause a second patient line to be no longer in fluid connection with the prime container and to only be in fluid connection with the first patient line;
after the first patient line is connected to the second patient line, sending instructions to the pump to cause the pump to run in reverse;
sending instructions to a level detector to detect a level of liquid in a vented chamber of the circuit, wherein a liquid entry port and a liquid exit port are in a bottom region of the chamber, and a filter is in a top region of the chamber; and
sending instructions to indicate that the priming sequence is complete upon receiving signals indicating that the level of liquid in the vented chamber has reached a desired level.

29. The computer program product of claim 28, wherein the clamping mechanism includes a plurality of valves.

30. The computer program product of claim 28, wherein the clamping mechanism includes a clamp.

31. The computer program product of claim 28, further comprising causing the data processing apparatus to perform operations comprising determining a pump reversal time, wherein sending instructions to the pump to cause the pump to run in reverse occurs at the pump reversal time.

32. The computer program product of claim 28, wherein determining a pump reversal time comprises receiving an actual flow rate and determining the pump reversal rate from the actual flow rate and a predetermined forward pumping volume.

33. The computer program product of claim 28, further comprising causing the data processing apparatus to perform operations comprising:
receiving instructions to begin pumping fluid from a patient;
in response to receiving the instructions to begin pumping fluid from a patient, sending instructions to the pump to run the pump; and
sending instructions to the clamping mechanism to open a connection between the second patient line and the prime container.

34. The computer program product of claim 33, further comprising causing the data processing apparatus to perform operations comprising:
receiving instructions to stop the pump after opening the connection between the second patient line and the prime container; and
sending instructions to the pump to stop the pump in response to the instructions to stop the pump.

* * * * *

UNITED STATES PATENT AND TRADEMARK OFFICE
CERTIFICATE OF CORRECTION

PATENT NO. : 7,892,197 B2
APPLICATION NO. : 11/858104
DATED : February 22, 2011
INVENTOR(S) : Thomas Irvin Folden It is certified that error appears in the above-identified patent and that said Letters Patent is hereby corrected as shown below:

Claim 10, column 12, line 31:
after "with" delete "a".

Signed and Sealed this
Tenth Day of May, 2011

David J. Kappos
*Director of the United States Patent and Trademark Office*